(12) United States Patent
Schreiner et al.

(10) Patent No.: US 11,273,144 B2
(45) Date of Patent: Mar. 15, 2022

(54) COMPOUNDS AND COMPOSITIONS FOR THE TREATMENT OF MUSCULAR DISORDERS AND BONE DISORDERS

(71) Applicant: Epirium Bio Inc., San Diego, CA (US)

(72) Inventors: George Frederic Schreiner, Los Altos Hills, CA (US); Guillermo Ceballos, Estado de Mexico (MX); Sundeep Dugar, San Jose, CA (US)

(73) Assignee: EPIRIUM BIO INC., San Diego, CA (US)

( * ) Notice: Subject to any disclaimer, the term of this patent is extended or adjusted under 35 U.S.C. 154(b) by 0 days.

(21) Appl. No.: 16/742,608

(22) Filed: Jan. 14, 2020

(65) Prior Publication Data

US 2020/0390741 A1    Dec. 17, 2020

Related U.S. Application Data

(63) Continuation of application No. 15/900,533, filed on Feb. 20, 2018, now abandoned, which is a continuation-in-part of application No. 14/387,117, filed as application No. PCT/US2013/033555 on Mar. 22, 2013, now Pat. No. 9,901,564.

(60) Provisional application No. 61/614,721, filed on Mar. 23, 2012.

(51) Int. Cl.
  *A61K 31/353* (2006.01)
  *A61P 19/08* (2006.01)
  *A61P 21/00* (2006.01)

(52) U.S. Cl.
  CPC ............ *A61K 31/353* (2013.01); *A61P 19/08* (2018.01); *A61P 21/00* (2018.01)

(58) Field of Classification Search
  CPC ......... A61K 31/353; A61P 21/00; A61P 19/08
  USPC ........................................................ 514/456
  See application file for complete search history.

(56) References Cited

U.S. PATENT DOCUMENTS

| | | |
|---|---|---|
| 6,312,753 B1 | 11/2001 | Kealey |
| 6,410,052 B1 | 6/2002 | Morre |
| 9,682,093 B2 | 6/2017 | Singh |
| 9,901,564 B2 | 2/2018 | Schreiner |
| 10,052,316 B2 | 8/2018 | Villarreal |
| 10,898,465 B2 | 1/2021 | Dugar |
| 2003/0180306 A1 | 9/2003 | Hill et al. |
| 2007/0015686 A1 | 1/2007 | Heuer |
| 2008/0317885 A1 | 12/2008 | Baker |
| 2010/0190733 A1 | 7/2010 | Squadrito |
| 2013/0171268 A1 | 7/2013 | Villarreal |
| 2015/0080328 A1 | 3/2015 | Villarreal |
| 2016/0120890 A1 | 5/2016 | Singh |
| 2018/0000908 A1 | 1/2018 | Mcdonagh et al. |
| 2018/0193306 A1 | 7/2018 | Schreiner |
| 2019/0046517 A1 | 2/2019 | Villarreal |
| 2019/0247359 A1 | 8/2019 | Dugar |
| 2019/0262347 A1 | 8/2019 | Dugar |
| 2020/0155533 A9 | 5/2020 | Villarreal et al. |

FOREIGN PATENT DOCUMENTS

| | | |
|---|---|---|
| CN | 100361655 C | 1/2008 |
| EP | 2022344 A1 | 2/2009 |
| EP | 2162747 B1 | 4/2014 |
| EP | 2875359 A2 | 5/2015 |
| EP | 2875359 A4 | 8/2015 |
| JP | 2004161669 A | 6/2004 |
| JP | 2005518381 A | 6/2005 |
| JP | 2011006355 A | 1/2011 |
| WO | 2003053336 A2 | 7/2003 |
| WO | 2003053336 A3 | 11/2003 |
| WO | 2007053642 A1 | 5/2007 |
| WO | 2010067953 A2 | 6/2010 |
| WO | 2010067953 A3 | 8/2010 |
| WO | 2010121232 A1 | 10/2010 |
| WO | 2012170430 A1 | 12/2012 |
| WO | 2013149258 A2 | 10/2013 |
| WO | 2013149258 A3 | 11/2013 |
| WO | 2013149258 A8 | 5/2014 |
| WO | 2015195701 A1 | 12/2015 |
| WO | 2017221269 A1 | 12/2017 |
| WO | 2018083713 A1 | 5/2018 |

OTHER PUBLICATIONS

Rondanelli et al. A Systematic Review on the Effects of Botanicals on Skeletal Muscle Health in Order to Prevent Sarcopenia. Evidence-Based Complementary and Alternative Medicine vol. 2016, Article ID 5970367, 23 pages, http://dx.doi.org/10.1155/2016/5970367 (Year: 2016).*

Kofink et al. Enantioseparation of catechin and epicatechin in plant food by chiral capillary electrophoresis. Eur Food Res Technol (2007) 225:569-577. (Year: 2007).*

Cacciottolo et al. Muscular dystrophy with marked Dysferlin deficiency is consistently caused by primary dysferlin gene mutations. European Journal of Human Genetics (2011) 19, 974-980. (Year: 2011).*

Ottaviani et al. The stereochemical configuration of flavanols influences the level and metabolism of flavanols in humans and their biological activity in vivo. Free Radical Biology & Medicine 50 (2011) 237-244. (Year: 2011).*

Yamashita et al. Prevention mechanisms of glucose intolerance and obesity by cacao liquor procyanidin extract in high-fat diet-fed C57BL/6 mice. Archives of Biochemistry and Biophysics 527 (2012) 95-104. (Year: 2012).*

(Continued)

*Primary Examiner* — Yih-Horng Shiao
(74) *Attorney, Agent, or Firm* — Morrison & Foerster LLP

(57) ABSTRACT

The present invention relates to compounds and compositions and their applications as pharmaceuticals for treating, preventing, or reversing injury to skeletal or cardiac muscles, for treating or preventing diseases relating to the structure and function of skeletal or cardiac muscle, and for inducing regeneration or restructuring of skeletal or cardiac muscle as a means of treating diseases relating to abnormalities in skeletal or cardiac muscle structure and function in a human or animal subject. Further aspects relate to the same or similar applications for bone and bone diseases.

38 Claims, 3 Drawing Sheets

(56) References Cited

OTHER PUBLICATIONS

Al-Zaidy, S.A. et al. (2015). "Follistatin Gene Therapy Improves Ambulation In Becker Muscular Dystrophy," J. of Neuromuscular Diseases 2:185-192.
Bäckman, E. et al. (Nov. 1998). "Selenium and Vitamin E Treatment of Duchenne Muscular Dystrophy: No Effect on Muscle Function," Acta Neurol. Scand. 78(5):429-435.
Damiano, S. et al. (Aug. 5, 2019). "Dual Role of Reactive Oxygen Species in Muscle Function: Can Antioxidant Dietary Supplements Counteract Age-Related Sarcopenia?" International J. of Molecular Sciences 20:3815, 18 pages.
Dugar, S. et al. (2020). "11-β-hydroxysterols as Possible Endogenous Stimulators of Mitochondrial Biogenesis as Inferred From Epicatechin Molecular Mimicyr," Pharmacological Research 151:104540, 11 pages.
Han, X. et al. (2019, e-pub. Aug. 11, 2019). "Mechanisms Involved in Follistatin-Induced Hypertrophy and Increased Insulin Action in Skeletal Muscle," Journal of Cachexia, Sarcopenia and Muscle 10:1241-1257.
Isaacs, J. et al. (2019). "Viral Vector Delivery of Follistatin Enhances Recovery of Reinnervated Muscle," Muscle & Nerve 60:476-485.
Ji, S. et al. (1999). "Soybean Isoflavones, Genistein and Genistin, Inhibit Rat Myoblast Proliferation, Fusion and Myotube Protein Synthesis," J. Nutr. 129:1291-1297.
McGreevy, J.W. et al. (Mar. 2015). "Animal Models of Duchenne Muscular Dystrophy: From Basic Mechanisms to Gene Therapy," Disease Models & Mechanisms 8(3):195-213, 47 pages.
Merry, T.L. et al. (2016). "Do Antioxidant Supplements Interfere With Skeletal Muscle Adaptation to Exercise Training?" J. Physiol. 594(18):5135-5147.
Timpani, C. et al. (2015). "Revisiting the Dystrophin-ATP Connection: How Half a Century of Research Still Implicates Mitochondrial Dysfunction in Duchenne Muscular Dystrophy Aetiology," Medical Hypotheses 85:1021-1033.
Van Bree, B.W.J. et al. (Mar. 14, 2016). "A Genistein-Enriched Diet Neither Improves Skeletal Muscle Oxidative Capacity Nor Prevents the Transition Towards Advanced Insulin Resistance in ZDF Rats," Scientific Reports 6:22854, 10 pages.
Velders, M. et al. (May 2010, e-pub. Mar. 27, 2010). "Estradiol and Genistein Antagonize the Ovariectomy Effects on Skeletal Muscle Myosin Heavy Chain Expression Via ER-beta Mediated Pathways," J. Steroid Biochem. Mol. Biol. 120(1)53-59.
Wagner, K.R. (2005). "Muscle Regeneration Through Myostatin Inhibition," Cur. Opin. Rheumatol. 17:720-724.
Yaden, B.C. et al. (May 2014). "Follistatin: A Novel Therapeutic for the Improvement of Muscle Regeneration," J. Pharmacol. Exp. Ther. 349:355-371, 25 pages.
Abd El-Aziz, T.A. et al. (2012, e-pub. Nov. 12, 2011). "Catechin protects against oxidative stress and inflammatory-mediated cardiotoxicity in adriamycin-treated rats," Clin Exp Med 12:233-240.
Ahmad, F. et al. (Jun. 1, 1991). "Effect of (-)Epicatechin On cAMP Content, Insulin Release and Conversion Of Proinsulin To Insulin In Immature And Mature Rat Islets In Vitro," Indian Journal Of Experimental Biology 29:516-520.
Chu C, et al. (Aug. 13, 2017). "Green Tea Extracts Epigallocatechin-3-Gallate for Different Treatments," BioMed 1 Research International 2017:Article 5615647, 9 pages.
Eijken, M. et al. (Sep. 2007, e-pub. Apr. 20, 2007). "Chapter 5: The Activin A-Follistatin System: Potent Regulator Of Human Extracellular Matrix Mineralization," FASEB J. 21(11):88-107.
Fechtner, S. et al. (2017, e-pub. May 19, 2017). "Molecular insights Into The Differences In Anti-Inflammatory Activities Of Green Tea Catechins On IL-1β Signaling In Rheumatoid Arthritis Synovial Fibroblasts," Toxicology and Applied Pharmacology 329:112-120.
Final Office Action, dated Feb. 10, 2020, for U.S. Appl. No. 15/900,533, filed Feb. 20, 2018, 18 pages.
Final Office Action, dated Oct. 20, 2016, for U.S. Appl. No. 14/387,117, filed Sep. 22, 2014, 13 pages.

Glossary of Medical Education Terms, Institute of International Medical Education retrieved from http://www.iime.org/glossary. htm, last visited Mar. 14, 2013, 23 pages.
Hansen, J. et al. (2011). "Exercise Induces A Marked Increase In Plasma Follistatin: Evidence That Follistatin Is A Contraction-Induced Hepatokine," Endocrinology 152:164-171.
Hongwei, S. et al. (Apr. 27, 2011). "Dietary Epicatechin Promotes Survival of Obese Diabetic Mice and Drosophila melanogaster," The Journal of Nutrition 141(6):1095-1100.
Hüttemann, M. et al. (Apr. 2012, e-pub. Dec. 16, 2011). "(-)-Epicatechin Maintains Endurance Training Adaptation In Mice After 14 Days Of Detraining," The FASEB Journal 26(4):1413-1422, 21 pages.
International Preliminary Report on Patentability, dated Aug. 27, 2020, for PCT Application No. PCT/US2019/018730, filed Feb. 20, 2019, 8 pages.
International Preliminary Report on Patentability, dated Sep. 23, 2014, for PCT Application No. PCT/US2013/033555, filed Mar. 22, 2013, 6 pages.
International Search Report and Written Opinion, dated Jul. 18, 2013, for PCT Application No. PCT/US2013/033555, filed Mar. 22, 2013, 10 pages.
International Search Report and Written Opinion, dated May 14, 2019, for PCT Application No. PCT/US2019/018730, filed Feb. 20, 2019, 10 pages.
Material Safety Data Sheet 855235, updated on Jun. 30, 2008. http://www.sigmaaldrich.com/MSDS/MSDS/DisplayMSDSPage.do?country=US&language=en&productNumber=855235&brand=ALDRICH&PageToGoToURL=http%3A%2F%2Fwww.sigmaaldrich.com%2Fcatalog%2Fproduct%2Faldrich%2F855235%3Fla ng%3Den, 5 pages.
Matzuk, M.M. et al. (Mar. 23, 1995). "Multiple Defects and Perinatal Death In Mice Deficient In Follistatin," Nature 374(6520):360-363.
Nagamine, T. et al (May 1998). "Immunochemical Detection Of Activin A, Follistatin, and Activing Receptors During Fracture Healing In The Rat," J Orthop. Res 16(3):314-321.
Nam, J. et al. (Sep. 2015, e-pub. Apr. 30, 2015). "Follistatin-like 3 Is A Mediator Of Exercise-Driven Bone Formation and Strengthening," Bone 78:62-70, 20 pages.
Nogueira, L. et al. (2011). "(-)-Epicatechin Enhances Fatigue Resistance And Oxidative Capacity In Mouse Muscle," The Journal of Physiology 589(18):4615-4631.
Non-Final Office Action, dated Apr. 7, 2017, for U.S. Appl. No. 14/387,117, filed Sep. 22, 2014, 19 pages.
Non-Final Office Action, dated Jun. 25, 2019, for U.S. Appl. No. 15/900,533, filed Feb. 20, 2018, 18 pages.
Non-Final Office Action, dated Mar. 25, 2016, for U.S. Appl. No. 14/387,117, filed Sep. 22, 2014, 16 pages.
Ottaviani, J.I. et al. (2011, e-pub. Nov. 11, 2010). "The Stereochemical Configuralion Of Flavanols Influences The Level and Metabolism Of Flavanols In Humans and Their Biological Activity In Vivo," Free Radical Biology & Medicine 50:237-244.
Remington's Pharmaceutical Sciences, Mack Publishing Company, Philadelphia, PA, 21th ed. (2000) TOC, 4 Pages.
Restriction Requirement, dated Nov. 10, 2015, for U.S. Appl. No. 14/387,117, filed Sep. 22, 2014, 11 pages.
Rondanelli, M. et al. (2016). "A Systematic Review on the Effects of Botanicals on Skeletal Muscle Health in Order to Prevent Sarcopenia," Evidence-Based Complementary and Alternative Medicine 2016:Article ID 5970367, 23 pages.
Shen, C.-L. et al. (2010). "Green Tea Polyphenols Mitigate Bone Loss Of Female Rats In A Chronic Inflammation-Induced Bone Loss Model," Journal of Nutritional Biochemistry 21:968-974.
Shen, C.-L. et al. (2013). "Tea and Bone Health: Steps Forward In Translational Nutrition," Am J Clin Nutr 98 (suppl):1694S-1699S.
Taub, P.R. et a. (Feb. 1, 2012, E-PUB. Nov. 7, 2011). "Alterations in Skeletal Muscle Indicators of Mitochondrial Structure and Biogenesis in Patients with Type 2 Diabetes and Heart Failure: Effects of Epicatechin Rich Cocoa," Clinical And Translational Science 5(1):43-47.
Testa, B. et al. (2003). Hydrolysis in Drug and Prodrug Metabolism: Chemistry, Biochemistry, and Enzymology Wiley VHCA, Zurich, Switzerland, TOC, 11 pages.

(56) References Cited

OTHER PUBLICATIONS

Wu, R.H. et al. (Oct. 21, 2001). "A Potential Indicator Of Denervated Muscle Atrophy: The Ratio Of Myostatin To Follistatin In Peripheral Blood," Genetics And Molecular Research 10(4):3914-3923.
Yamazaki, K.G. et al. (2008, e-pub. Jun. 20, 2008). "Short-and Long-Term Effects Of (-)-Epicatechin On Myocardial Ischemia-Reperfusion Injury," Am J Physiol Heart Circ. Physiol 295:H761-H767.
Ahmad, S.S. et al. (Jul. 24, 2020). "Implications of Insulin-Like Growth Factor-1 In Skeletal Muscle and Various Diseases," Cells 9:1773, 15 pages.
Declaration of George Schreiner (Aug. 4, 2017), 6 pages.
Declaration of George Schreiner (Jul. 22, 2016), 14 pages.
Gomez-Cabrera, M. et al. (2008) "Oral Administration of Vitamin C Decreases Mitochondrial Biogenesis and Hampers Training-Induced Adaptations In Endurance Performance," Am. J. Clin. Nutr. 87:142-149.
Gutierrez-Salmean, G. et al. (Nov. 2016, e-pub. Aug. 8, 2016). "A Randomized, Placebo-Controlled, Double-Blind Study On The Effects of (-)-Epicatechin On The Triglyceride/HDLc Ratio and Cardiometabolic Profile of Subjects With Hypertriglyceridemia: Unique in vitro Effects," Int. J. Cardiol 223:500-506. Abstract Only.
Kota, J. et al. (Nov. 11, 2009). "Follistatin Gene Delivery Enhances Muscle Growth and Strength in Nonhuman Primates," Sci. Transl. 1(6):6ra15, 9 pages.
Kuo, T. et al. (2015) "Regulation of Glucose Homeostasis by Glucocortiocoids," Adv. Exp Med. Biology 872:99-126, 30 pages.
Matthews, E. et al. (2016). "Corticosteroids For The Treatment of Duchenne Muscular Dystrophy," Cochrane Library 5(CD003725):1-116.
McDonald, C.M. et al. (2020). "(-)-Epicatechin Induces Mitochondrial Biogenesis and Markers of Muscle Regeneration in Adults with Becker Muscular Dystrophy," Muscle & Nerve 1:1-11.
McKay, B. et al. (2008, e-pub. Sep. 25, 2008). "Co-Expression of IGF-1 Family Members With Myogenic Regulatory Factors Following Acute Damaging Muscle-Lengthening Contractions in Humans," J. Physiol 586 (22):5549-5560.
Merck's Online Catalogue Entry for Epicatechin, (2021). 4 pages.
Rodino-Klapac, L.R. et al. (2013, e-pub. Jul. 17, 2013). "Micro-Dystrophin and Follistatin Co-Delivery Restores Muscle Function in Ages DMD Model," Human Molecular Genetics 22(24):4929-4937.
Sriram, S. et al. (Aug. 16, 2011). "Modulation of Reactive Oxygen Species In Skeletal Muscle By Myostatin Is Mediated Through NFκB: Myostatin Induces Reactive Oxygen Species," Aging Cell 10(6):931-948.
Zhang, H. et al. (Jan. 14, 2016). "The Protective Effect of Epicatechin on Experimental Ulcerative Colitis in Mice is mediated By Increasing Antioxidation and By The Inhibatiion of NF-κB Pathway," Pharmacol. Rep. Abstract Only, 2 pages.
Sumner, C.J. et al. (Jan. 1, 2017). "Spinal Muscular Atrophy—Disease Mechanism and Therapy/PASSAGE/," in Spinal Muscular Atrophy—Disease Mechanism and Therapy, 14 pages.
Usmani, A. et al. (Jan. 1, 2016). "An Amazing Herb With Extraordinary Payback: Camellia sinensis," Research & Reviews: A Journal of Pharmacology 6(2):1-11.

\* cited by examiner

Group 1 - Vehicle Control  Group 2 - Dexa - 0.5 MPK s/c  Group 3 - SPR105590 - 3 MPK s/c  Group 4 - SPR105590 - 10 MPK s/c

COMPOUNDS AND COMPOSITIONS FOR THE TREATMENT OF MUSCULAR DISORDERS AND BONE DISORDERS

This application is a continuation of U.S. patent application Ser. No. 15/900,533, filed Feb. 20, 2018, which is a continuation in part of U.S. patent application Ser. No. 14/387,117, filed Sep. 22, 2014, now U.S. Pat. No. 9,901,564 which is the 371 national stage filing of PCT/US2013/033555, filed Mar. 22, 2013, which claims the benefit of U.S. Provisional Patent Application No. 61/614,721, filed Mar. 23, 2012, the disclosures of which are hereby incorporated by reference as if written herein in their entireties.

Disclosed herein are compounds and compositions and their application as pharmaceuticals for treating, preventing, or reversing injury to skeletal or cardiac muscles, for treating or preventing diseases relating to the structure and function of skeletal or cardiac muscle, and for inducing regeneration or restructuring of skeletal or cardiac muscle as a means of treating diseases relating to abnormalities in skeletal or cardiac muscle structure and function in a human or animal subject. Also disclosed herein are methods for diagnosing injury to skeletal or cardiac muscle and for diagnosing the success or failure of therapeutics designed to treat, prevent, or reverse injury to skeletal muscle or cardiac muscle.

Strength and endurance of skeletal muscle is essential for gripping, carrying, walking, running, carrying or enabling numerous functions of everyday life. Strength and endurance of cardiac muscle is essential for the optimum delivery of oxygen and nutrients to all tissues containing blood vessels and for the carrying away of waste products of cell metabolism. Injury to skeletal or cardiac muscle or diseases relating to abnormal structure or function of skeletal or cardiac muscle can make normal activities of everyday life difficult or impossible.

Further, injury to, or weakness of, skeletal muscle generally results in a loss of bone density in the bones to which that muscle is attached. In the case of generalized muscle weakness, reduction in bone density can be generalized, one of the causes of the bone disease known as osteoporosis.

Injury to skeletal or cardiac muscle can occur as a result of genetic mutations in proteins critical to the structure and function of skeletal muscle or cardiac muscle, inadequate or interrupted blood flow, inactivity due to joint injury or inflammation, as is seen with arthritis, excessive exposure to oxidation injury as a result of defective cell metabolism or inadequate blood flow, exposure to toxic organic or inorganic substances such as elevated glucose, heavy metals, or inflammatory products, trauma due to injury or excessive activity, or exposure to certain medications such as statins, corticosteroids, or chemotherapy, among other causes. Examples of inflammatory diseases associated with muscle disorders include polymyositis, polymyalgia rheumatic a, and systemic lupus erythematosus.

Injury to skeletal muscle and consequent weakness or atrophy can occur as a result of injury or disorders of the neurons subserving muscle function. Appropriate innervation is essential to skeletal muscle health and function. Neurodegenerative diseases amenable to treatment with agents stimulating muscle strength and neuromuscular health include amyotrophic lateral sclerosis (ALS), Parkinson's disease, Huntington's disease, spinal cord injury or abnormality, and peripheral and central neuropathies.

Currently therapies emphasize prevention, such as use of stents to improve blood flow through areas of vascular narrowing. There are general supportive interventions to help the muscle repair itself, such as the nutritional provision of muscle protein precursors such as amino acids or creatine. Current therapies may address the underlying disorder associated with cardiac or skeletal muscle dysfunction without directly treating the muscle cells themselves. The only accepted therapy directed at the muscles themselves is exercise. It has been demonstrated that regular, moderate activation of muscle cells can improve the structure and function of cardiac and skeletal muscle cells. However, this is often inadequate in restoring muscle cell health or function.

Complicating the potential therapies is the fact that neither skeletal muscle nor cardiac muscle cells are capable of sufficient proliferation in order to replace muscle cells previously damaged or destroyed. There may be some limited capacity of stem cells to proliferate but this is not generally sufficient to regenerate functionally significant replacement muscle. Skeletal muscle is known to contain primitive satellite cells, which can activate, enlarge, and differentiate into skeletal muscle tissue. The role of satellite cells in replacing cardiac cells is currently not well understood. Repair of muscles is enhanced by muscle cellular expression of follistatin, which allows for activation and differentiation of muscle precursor cells into mature, differentiated skeletal muscle cells. Repair of muscle cells or generation of new, differentiated muscle cells is inhibited by the expression of a negative regulatory factor known as myostatin.

Disclosed herein are methods for prophylactic and/or therapeutic treatment of skeletal or cardiac muscle dysfunction, injury, or diseases in a patient by administering epicatechin, an epicatechin derivative, a pharmaceutically acceptable salt or prodrug thereof, or combinations thereof. The methods and compositions described herein can assist in prevention of impaired skeletal and cardiac muscle function, recovery of skeletal or cardiac muscle health or function, or functionally significant regeneration of skeletal or cardiac muscle cells or function.

In certain embodiments, the present invention comprises administering a compound or composition disclosed herein in an amount effective to stimulate function, recovery, or regeneration of skeletal or cardiac muscle cells. Stimulation of muscle cell function, recovery, or regeneration may comprise increased expression of one or more of proteins having contractile, regulatory, transcriptional, or attachment functions. Stimulation of muscle cell function, recovery, or regeneration may comprise increased mitochondrial number and function. In certain embodiments, the compound or composition comprises a therapeutically effective amount of epicatechin, either (+) or (−) enantiomers or a combination of both, an epicatechin derivative, or a pharmaceutically acceptable salt or prodrug thereof.

In further embodiments, the present invention provides methods and compositions for preventing or treating adverse events or diseases associated with impaired skeletal muscle or cardiac muscle cell number or function. The methods comprise administering to a subject in need thereof one or more compounds or compositions disclosed herein. In further embodiments the method reduces symptoms of impaired skeletal or cardiac muscle cell number or function. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In certain embodiments, disclosed herein are methods and compositions for the treatment of diseases associated with loss of number, function, or correct, optimally efficient internal organization of skeletal muscle cells or cardiac muscle cells. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In further embodiments, disclosed herein are methods and compositions for the treatment of impaired skeletal or cardiac muscle function due to aging, obesity, disuse or inactivity, exposure to potentially toxic nutritional agents such as fructose, or exposure to inadequate nutrition such as starvation or malnutrition. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In further embodiments, disclosed herein are methods and compositions for the treatment of muscle-related side effects of athletic training or competition including soreness, cramping, weakness, pain, or injury. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In further embodiments, disclosed herein are methods and compositions for the treatment of skeletal or cardiac muscle diseases associated with ischemia, or impaired or inadequate blood flow. Examples of such states include, but are not limited to, atherosclerosis, trauma, diabetes, vascular stenosis, peripheral arterial disease, vasculopathy, and vasculitis. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In further embodiments, disclosed herein are methods and compositions for the treatment of diseases associated with genetic disorders that directly or indirectly affect the number, structure, or function of cardiac muscle cells or skeletal muscle cells. Examples of such states include, but are not limited to, the set of diseases broadly classified as muscular dystrophies and Friedreich's ataxia. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In further embodiments, disclosed herein are methods and compositions for the therapeutic treatment of diseases associated with impaired neurological control of muscular activity resulting in consequent abnormalities in structure and function of skeletal muscles due to inactivity, aberrant contractility, or contracted states. These include, but are not limited to, states associated with absent, diminished, or abnormal neurological activity including peripheral denervation syndromes, trauma, amyotrophic lateral sclerosis, meningitis, and structural abnormalities of the spine, whether congenital or acquired. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In certain embodiments, disclosed herein are methods and compositions for the treatment of diseases associated with loss of number, loss of function, or loss of correct, optimally efficient internal organization of skeletal muscle cells or cardiac muscle cells. Such diseases may eventuate in a state of functionally significant muscle wasting, which, in its most pronounced form, is termed sarcopenia. Sarcopenia may be secondary to a variety of disorders, including aging, diabetes or other abnormal metabolic conditions, infection, inflammation, autoimmune disease, cardiac dysfunction, or severe disuse syndromes or inactivity associated with arthritis. Examples of such diseases include, but are not limited to, congestive heart failure, aging, myocarditis, myositis, polymyalgia rheumatic, polymyositis, HIV, cancer and/or the side effects of chemotherapy targeting the cancer, malnutrition, aging, inborn errors of metabolism, trauma, and stroke or other types of neurological impairment. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In certain embodiments, disclosed herein are methods and compositions for use in combination with exercise or programmatic sequences or intensities of exercise to optimize methods for the prophylactic or therapeutic treatment of diseases or disorders associated with loss of number, loss of function, or loss of correct, optimally efficient internal organization of skeletal muscle or cardiac muscle cells. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In certain embodiments, disclosed herein are methods and compositions for use to enhance sports performance and endurance, to build muscle shape and strength, and to facilitate recovery from the muscle related side effects of training or competition, such as soreness, weakness, cramping, pain, or injury. In certain embodiments, the method comprises administering, or the composition comprises, a therapeutically effective amount of epicatechin, either (+) or (−) enantiomers or a combination of both, an epicatechin derivative, or a pharmaceutically acceptable salt or prodrug thereof.

In certain embodiments, disclosed herein are methods and compositions for use to prevent, ameliorate, or reverse muscle injury, weakness, or pain associated with the administration of certain medicines, including, but not limited to, corticosteroids such as prednisone, methyl prednisone, or halogenated derivatives thereof, chemotherapeutics such as doxorubicin or methotrexate, and inhibitors of HMG co-reductase, known as statins, that are frequently associated with muscle disorders or myopathy, including: Advicor™ (niacin extended-release/lovastatin), Altoprev™ (lovastatin extended-release), Caduet™ (amlodipine and atorvastatin), Crestor™ (rosuvastatin), Juvisync™ (sitagliptin/simvastatin), Lescol™ (fluvastatin), Lescol XL (fluvastatin extended-release), Lipitor™ (atorvastatin), Compactin (mevastatin), Livalo® (pitavastatin), Mevacor™ (lovastatin), Pravachol™ (pravastatin), Simcor™ (niacin extended-release/simvastatin), Vytorin™ (ezetimibe/simvastatin), and Zocor™ (simvastatin). In certain embodiments, the method comprises administering, or the composition comprises, a therapeutically effective amount of epicatechin, either (+) or (−)

enantiomers or a combination of both, an epicatechin derivative, or a pharmaceutically acceptable salt or prodrug thereof.

In certain embodiments, disclosed herein are methods and compositions for use to prevent, ameliorate, or reverse muscle injury associated with medicines that damage mitochondria and/or cause myopathy as a secondary consequence.

In certain embodiments, a subject is selected for treatment with a compound or composition disclosed herein based on the occurrence of one or more physiological manifestations of skeletal or cardiac muscle injury or dysfunction in the subject. Such manifestations include elevations in biomarkers known to be related to injury of the heart or skeletal muscle. Examples of such biomarkers include, but are not limited to, elevated plasma levels of cardiac or skeletal muscle enzymes or proteins, such as myoglobin, troponin, or creatine phosphokinase, lactic acidosis, and elevated serum creatinine.

In certain embodiment, a compound or composition as disclosed herein is administered in an amount which stimulates increased number or function of skeletal muscle cells or contractile muscle cells. Such stimulation of muscle cells may comprise stimulation of one or more aspects of muscle cell function, including cell division, muscle cell regeneration, activation of muscle satellite cells and their differentiation into adult muscle cells, recovery from injury, increased number or function of mitochondria or processes serving mitochondrial function, increased expression of proteins contributing to contractility, regulation of biochemical or translational processes, mitoses, or transduction of mechanical energy via dystrophin or other attachment processes. The methods and compositions described herein can assist in prevention of the consequences of muscle injury or dysfunction which have not yet occurred, as well as provide for the active therapy of muscle injury, dysfunction, or diseases which have already occurred.

In certain embodiments, disclosed herein are methods to utilize the muscle proteins whose expression is stimulated by administration of compounds or compositions disclosed herein as diagnostic biomarkers by which to determine the time and degree of muscle response to the therapeutic methods and compositions disclosed herein. Such biomarkers may be determined by measuring in tissue, plasma, blood, or urine the proteins themselves or the DNA or RNA nucleotides that encode for the proteins. In one embodiment, a decrease in the body of useful muscle proteins, such as dystrophin, or the presence of inhibitory proteins, such as thrombospondin, may be used to diagnose the severity of the abnormality of cardiac muscle structure or function or the probability of response to the therapeutic methods and compositions described herein. In another embodiment, changes in the levels of such biomarkers may be used to gauge the success or failure of certain therapeutic modalities, including those disclosed herein, in order to optimize the dose and to decide whether to maintain or change therapeutic methods and compositions.

In another embodiment, an increase in the plasma concentration of follistatin, or a decrease in myostatin, or an increase in the ratio of plasma follistatin to plasma myostatin, may be used as a diagnostic method to diagnose the degree of severity of a muscle disorder or the extent of response to therapy.

In certain embodiments, the methods disclosed herein comprise the administration to cells at least 0.1) IM epicatechin or an epicatechin derivative, at least 0.25) IM epicatechin or an epicatechin derivative, at least 0.5) IM epicatechin or an epicatechin derivative, and at least 1) IM epicatechin or an epicatechin derivative.

In further embodiments, the methods disclosed herein comprise the administration of compounds of the disclosure in a total daily dose of about 0.1 mg/kg/dose to about 100 mg/kg/dose, alternately from about 0.3 mg/kg/dose to about 30 mg/kg/dose. In another embodiment the dose range is from about 0.5 to about 10 mg/kg/day. Alternately about 0.5 to about 1 mg/kg/day is administered. Generally between about 25 mg and about 1 gram per day can be administered; alternately between about 25 mg and about 200 mg can be administered. The dose may be administered in as many divided doses as is convenient.

In further embodiments, the methods disclosed herein comprise the administration of epicatechin, an epicatechin derivative, or a mixture thereof in a range of about 1 to about 1000 mg per kg body weight, about 1 to about 50 mg per kg body weight, or about 10 to about 100 mg per kg body weight of said subject.

In further embodiments, the desired concentration is maintained for at least 30 minutes, 1 hour, 3 hours, 6 hours, 12 hours, 24 hours, 48 hours, 72 hours, or more. In yet further embodiments, the desired concentration is achieved at least once during each 12-hour period over at least 24 hours, 48 hours, 72 hours, 1 week, one month, or more; or at least once during each 24-hour period over at least 48 hours, 72 hours, 1 week, one month, or more. In order to maintain a desired concentration for a desired time, multiple doses of one or more compounds may be employed. The dosing interval may be determined based on the clearance half-life for each compound of interest from the body.

In certain embodiments, the epicatechin or epicatechin derivative administered in a method disclosed herein is at least 90% pure relative to other compounds selected from the group consisting of epicatechin, an epicatechin derivative, catechin, or a catechin derivative. For example, if the compound is epicatechin, it contains no more than 10% contamination with epicatechin derivatives, catechin, and catechin derivatives. In further embodiments the selected epicatechin or epicatechin derivative is at least 95% pure relative to other compounds selected from the group consisting of epicatechin, an epicatechin derivative, catechin, or a catechin derivative. It is noted that this does not exclude combination with an additional therapeutic agent in substantial concentration.

In further embodiments, said epicatechin is (−)-epicatechin.

In further embodiments, said epicatechin is (+)-epicatechin.

In further embodiments, said epicatechin is a racemic mixture of (−)-epicatechin and (+)-epicatechin.

Also disclosed herein is a novel class of compounds that are the only known agents that, when administered, induce the production of circulating follistatin in the body of animals and humans. Follistatin and its closely homologous (80% sequence homology) family of follistatin-like proteins are produced by numerous cell types in the body, including muscle cells and bone cells. Follistatin is known to induce muscle regeneration in various disease states. Follistatin-like protein 3 has recently been shown to stimulate bone regeneration and increase mechanical bone strength in exercise. See J Nam et. Al. Follistatin-like 3 is a mediator of exercise-driven bone formation and strengthening. *Bone* 2015 78:62-70 doi:10.1016/j.bone.2015.04.038. Exercise, which strengthens both muscle and bone, induces increased plasma levels of follistatin and its related, follistatin-like proteins. See Hansen J et al. Exercise induces a marked increase in plasma follistatin: evidence that follistatin is a contraction-induced hepatokine. 2011 Endocrinology 152:164-171 Pub Med 21068158. Animals lacking follistatin display weak skeletal bone formation and profound muscle weakness. See Matzuk, M M et al. Multiple defects and perinatal death in mice deficient in follistatin. *Nature* 1995 374:360-3. PubMed 7885475. Production of extracellular matrix and its mineralization are the essential components of new bone formation by osteoblasts. Follistatin stimulates both activities in cultures of human osteoblasts. See Eijken et al, The activin A-follistatin system: potent regulator of human extracellular matrix mineralization Faseb J 2007 21:2949-60. During the healing of bone fractures, the expression of follistatin and its receptors are strongly increased in the periosteum near the ends of the bone fractures, indicating that follistatin is contributing to the formation and remodeling of bone during fracture healing. See Nagame T et al Immunochemical detection of activin A, follistatin, and activin receptors during fracture healing in the rat J Orthop Res 1998 16:314-21. Thus any agent that stimulates follistatin production should be therapeutic in the context of the numerous diseases, conditions, drug side effects, and genetic defects that contribute to the development of osteoporosis and its attendant increased risk of bone fractures.

Some embodiments relate to a method to induce increased cellular or muscular or bodily production of follistatin and follistatin-like proteins in order to reverse or ameliorate injury to, or weakness of, or loss of, bone, or to prevent fractures, in a subject in need thereof, comprising administering to a subject a therapeutically effective dose of (+)-epicatechin and/or (−)-epicatechin or an epicatechin derivative of either (+)-epicatechin or (−)-epicatechin. In further embodiments, the (+)-epicatechin and/or (−)-epicatechin or an epicatechin derivative is administered orally or intravenously or intramuscularly, at 5 mg to 2 grams per day, in a single dose or in divided doses. In other embodiments, the (+)-epicatechin and/or the (−)-epicatechin or an epicatechin derivative is administered at a dose between 0.1 mg/kg of bodyweight per day to 10 mg/kg of bodyweight per day, orally or intravenously or intramuscularly, in a single dose or in divided doses. In still other embodiments, the method induces new bone formation or additional bone formation or stronger bone formation or regeneration of bone in order to prevent bone fractures.

Additional embodiments disclosed herein relate to a method to induce the increased cellular or muscular or bodily production of follistatin and follistatin-like proteins in order to reverse or ameliorate weakness of bone, thus preventing bone fractures, caused by administration of compounds known to induce weakness of or damage to bone, impairment of bone generation, or impairment of bone growth, including but not limited to corticosteroids such as prednisone, or deflazacort, anticonvulsants such as phenytoin and phenobarbital, chemotherapeutics such as aromatase inhibitors, and progestins. Further method aspects relate to a to induce the increased cellular or muscular or bodily production of follistatin or follistatin-like proteins in order to reverse or ameliorate weakness of bone strength, thus preventing bone fractures, associated with genetic predisposition, aging, inactive lifestyle, or low estrogen states such as menopause or post oophorectomy; a method to induce the increased cellular or muscular or bodily production of follistatin or follistatin-like proteins in order to reverse or ameliorate weakness of bone caused by medical conditions known to be associated with weakness of, or damage to, bone, impairment of bone generation, or impairment of bone growth, such as celiac disease, kidney or liver disease, and inflammatory diseases such as systemic lupus erythematosus and rheumatoid arthritis; a method to induce the increased cellular or muscular or bodily production of follistatin or follistatin-like proteins in order to reverse or ameliorate weakness of bone in conjunction with the administration of other agents used to treat osteoporosis including calcium, Vitamin D, and calcitonin, in order to prevent bone fractures; a method to induce increased cellular or muscular or bodily production of follistatin or follistatin-like proteins as a therapeutic to accelerate the healing of bone fractures or to increase the degree of recovery from a bone fracture, such as those experienced in accidents, athletics, or combat; and a method to induce increased cellular or muscular or bodily production of follistatin or follistatin-like proteins in order to prevent systemic loss of bone density, and thus prevent subsequent bone fractures, during the recovery period after orthopedic surgery or after the onset of a disease or condition necessitating long periods of bed rest or physical inactivity, which are known to result in decreased bone density and muscle weakness.

In any of the aforementioned method embodiments, it is contemplated that the (+)-epicatechin and/or (−)-epicatechin or an epicatechin derivative may optionally be administered orally or intravenously or intramuscularly; at 5 mg to 2 grams per day; and/or in a single dose or in divided doses.

DETAILED DESCRIPTION

Figure 1:
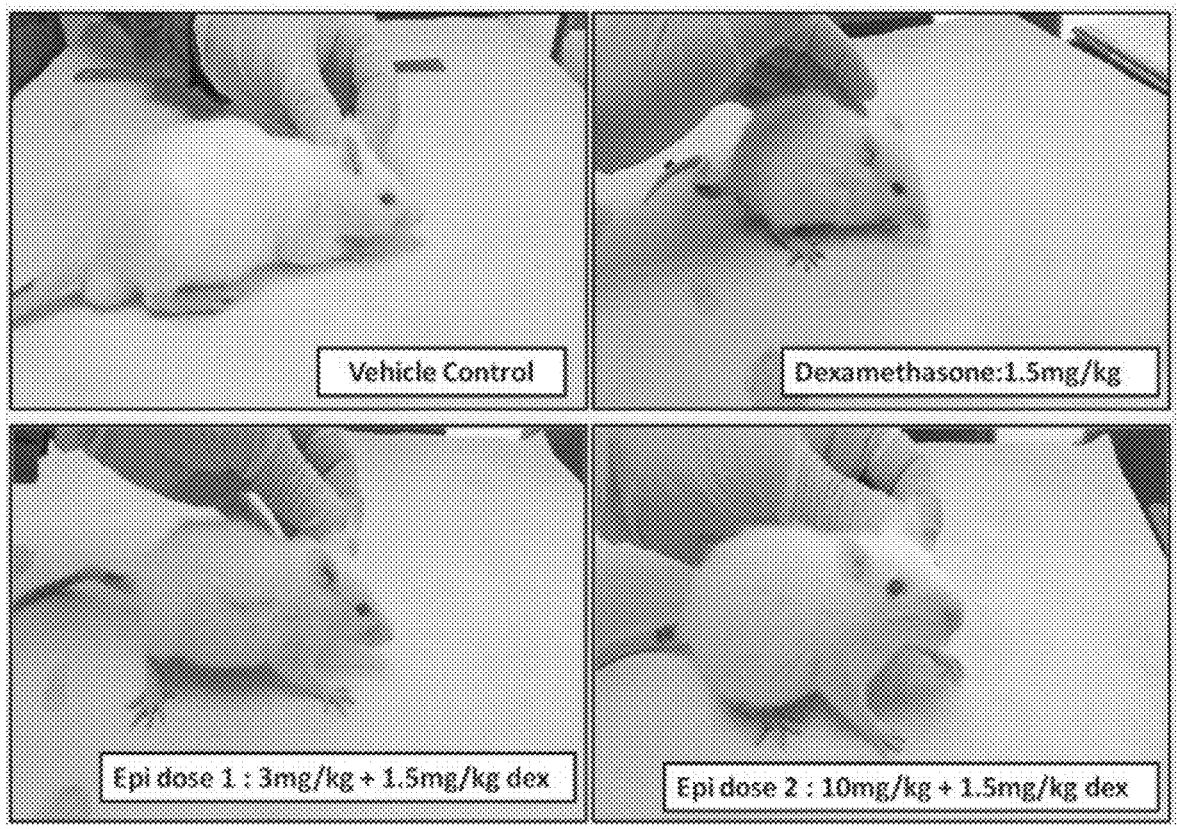
FIG. 1 shows pictures of mice in the various treatment groups.
Figure 2:
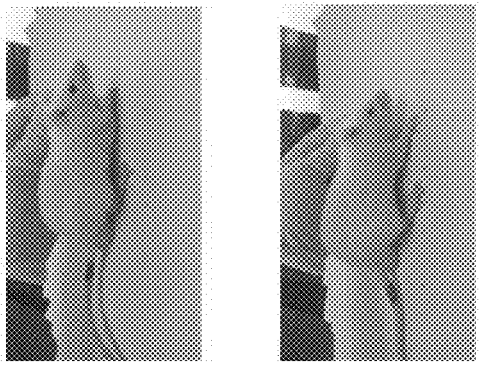
FIG. 2 shows additional pictures of mice in the various treatment groups.
Figure 2:
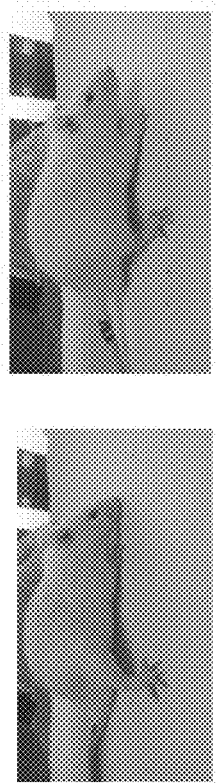
Figure 2:
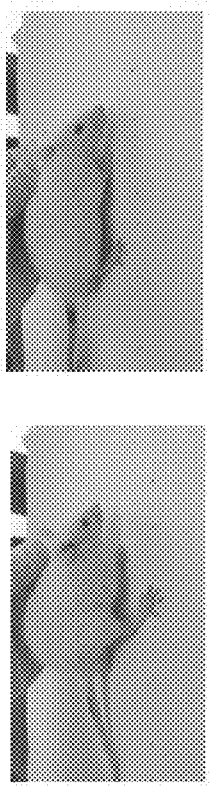
Figure 2:
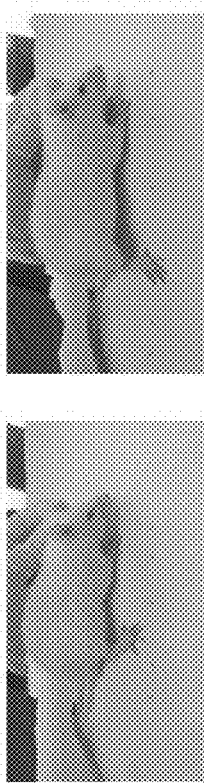
Figure 2:
Figure 3:
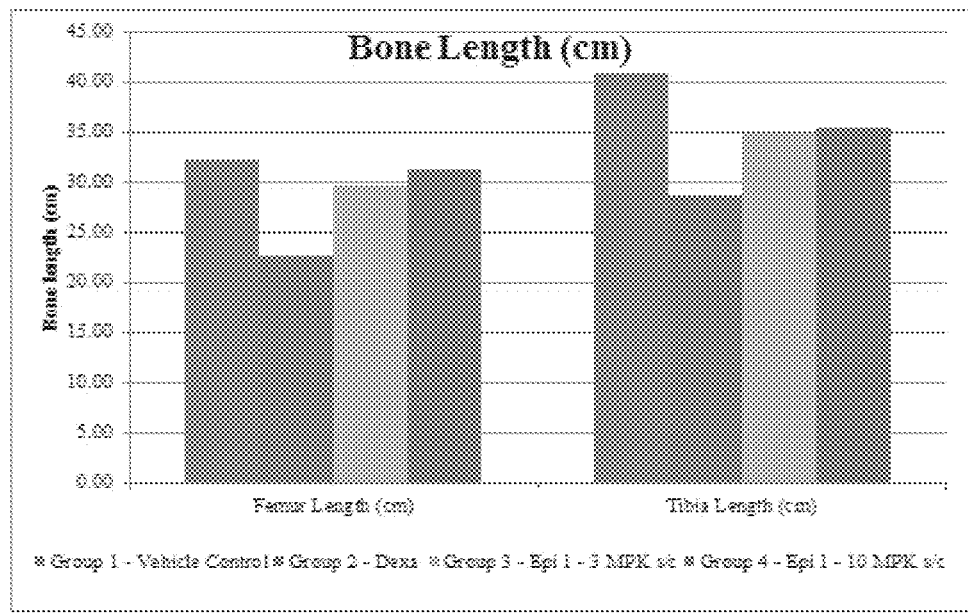
FIG. 3 depicts a chart of bone length in four different treatment groups.

Accordingly, provided herein is a method of treating, preventing, or reversing injury to skeletal or cardiac muscles, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for treating, preventing, or reversing injury to skeletal or cardiac muscles, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof.

Also provided is a method of treating a disease relating to an impaired skeletal or cardiac muscle structure or function of skeletal or cardiac muscle, comprising the administration of a therapeutically effective amount of epicatechin, either (+) or (−) enantiomers or a combination of both an epicatechin derivative, a pharmaceutically acceptable salt or prodrug thereof, or combinations thereof to a patient in need thereof. Also provided is a composition for treating, preventing, or reversing injury to skeletal or cardiac muscles, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

In certain embodiments, said impairment is due to aging, obesity, disuse or inactivity, exposure to potentially toxic nutritional agents such as fructose, or exposure to inadequate nutrition such as starvation or malnutrition.

Also provided herein is a method of inducing regeneration or restructuring of skeletal or cardiac muscle, comprising the administration of a therapeutically effective amount of epicatechin, either (+) or (−) enantiomers or a combination of both an epicatechin derivative, a pharmaceutically acceptable salt or prodrug thereof, or combinations thereof to a patient in need thereof. Also provided is a composition for inducing regeneration or restructuring of skeletal or cardiac muscle, comprising a therapeutically effective amount of epicatechin, either (+) or (−) enantiomers or a combination of both an epicatechin derivative, a pharmaceutically acceptable salt or prodrug thereof, or combinations thereof to a patient in need thereof.

Also provided herein is a method of diagnosing injury to skeletal or cardiac muscle and for diagnosing the success or failure of therapeutics designed to treat, prevent, or reverse injury to skeletal muscle or cardiac muscle, comprising:
 a. observing one or more physiological manifestations of skeletal or cardiac muscle injury or dysfunction in the subject;
 b. administering a therapeutically effective amount of epicatechin, either (+) or (−) enantiomers or a combination of both, an epicatechin derivative, a pharmaceutically acceptable salt or prodrug thereof, or combinations thereof to a patient in need thereof; and
 c. observing a change or lack thereof in said physiological manifestations of skeletal or cardiac muscle injury or dysfunction.

Also provided herein is a method of improving muscle cell function, recovery, or regeneration, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for improving muscle cell function, recovery, or regeneration, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

In certain embodiments, improving of muscle cell function, recovery, or regeneration comprises increased mitochondrial number and function.

Also provided herein is a method of treating muscle-related side effects of athletic training or competition including soreness, cramping, weakness, pain, or injury, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for treating muscle-related side effects of athletic training or competition including soreness, cramping, weakness, pain, or injury, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

Also provided herein is a method of treating skeletal or cardiac muscle diseases associated with ischemia or impaired or inadequate blood flow, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for treating skeletal or cardiac muscle diseases associated with ischemia or impaired or inadequate blood flow, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

In certain embodiments, said diseases are selected from the group consisting of atherosclerosis, trauma, diabetes, vascular stenosis, peripheral arterial disease, vasculopathy, and vasculitis.

Also provided herein is a method of treating a disease associated with genetic disorders that directly or indirectly affect the number, structure, or function of cardiac muscle cells or skeletal muscle cells, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for treating diseases associated with genetic disorders that directly or indirectly affect the number, structure, or function of cardiac muscle cells or skeletal muscle cells, comprising therapeutically effective amount of epicatechin, either (+) or (−) enantiomers or a combination of both, an epicatechin derivative, a pharmaceutically acceptable salt or prodrug thereof, or combinations thereof to a patient in need thereof.

In certain embodiments, said diseases are selected from the group consisting of muscular dystrophies and Friedreich's ataxia.

Also provided herein is a method of treating diseases associated with impaired neurological control of muscular activity resulting in consequent abnormalities in structure and function of skeletal muscles due to inactivity, aberrant contractility, or contracted states, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for treating diseases associated with impaired neurological control of muscular activity resulting in consequent abnormalities in structure and function of skeletal muscles due to inactivity, aberrant contractility, or contracted states, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

In certain embodiments, said diseases are selected from the group consisting of peripheral denervation syndromes, trauma, amyotrophic lateral sclerosis, meningitis, and structural abnormalities of the spine.

Also provided herein is a method of treating diseases associated with loss of number, loss of function, or loss of correct, optimally efficient internal organization of skeletal muscle cells or cardiac muscle cells, comprising the administration of a therapeutically effective amount of epicatechin, either (+) or (−) enantiomers, or a combination of both, an epicatechin derivative, a pharmaceutically acceptable salt or prodrug thereof, or combinations thereof to a patient in need thereof. Also provided is a composition for treating diseases associated with loss of number, loss of function, or loss of correct, optimally efficient internal organization of skeletal muscle cells or cardiac muscle cells, comprising a therapeutically effective amount of epicatechin, either (+) or (−) enantiomers, or a combination of both, an epicatechin derivative, a pharmaceutically acceptable salt or prodrug thereof, or combinations thereof to a patient in need thereof.

In certain embodiments, said disease is muscle wasting.

In certain embodiments, said disease is sarcopenia.

In certain embodiments, said sarcopenia is associated with aging, diabetes, abnormal metabolic conditions, infection, inflammation, autoimmune, disease, cardiac dysfunction, arthritis congestive heart failure, aging, myocarditis, myositis, polymyalgia rheumatic, polymyositis, HIV, cancer, side effects of chemotherapy, malnutrition, aging, inborn errors of metabolism, trauma, stroke, and neurological impairment.

In certain embodiments, the method of treating diseases associated with loss of number, loss of function, or loss of correct, optimally efficient internal organization of skeletal muscle cells or cardiac muscle cells further comprises exercise or programmatic sequences or intensities of exercise.

Also provided herein is a method of enhancing sports performance, endurance, building muscle shape or strength, or facilitating recovery from the effects of training or competition, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for enhancing sports performance, endurance, building muscle shape or strength, or facilitating recovery from the effects of training or competition, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

Also provided herein is a method of treating muscle injury, weakness, or pain associated with the administration of medicines, comprising the administration of a therapeutically effective amount of epicatechin, either (+) or (−) enantiomers or a combination of both, an epicatechin derivative, a pharmaceutically acceptable salt or prodrug thereof, or combinations thereof to a patient in need thereof. Also provided is a composition for treating muscle injury, weakness, or pain associated with the administration of medicines, comprising a therapeutically effective amount of epicatechin, either (+) or (−) enantiomers or a combination of both, an epicatechin derivative, a pharmaceutically acceptable salt or prodrug thereof, or combinations thereof to a patient in need thereof.

In certain embodiments, said medicine is selected from the group consisting of corticosteroids such as prednisone, methyl prednisone, or halogenated derivatives thereof, chemotherapeutics such as doxorubicin or methotrexate, and inhibitors of HMG co-reductase, known as statins, that are frequently associated with muscle disorders or myopathy, including: Advicor™ (niacin extended-release/lovastatin), Altoprev™ (lovastatin extended-release), Caduet™ (amlodipine and atorvastatin), Crestor™ (rosuvastatin), Juvisync™ (sitagliptin/simvastatin), Lescol® (fluvastatin), Lescol XL (fluvastatin extended-release), Lipitor™ (atorvastatin), Compactin (mevastatin), Livalo® (pitavastatin), Mevacor™ (lovastatin), Pravachol™ (pravastatin), Simcor™ (niacin extended-release/simvastatin), Vytorin™ (ezetimibe/simvastatin), and Zocor® (simvastatin).

In certain embodiments of anyone of the embodiments disclosed above, said epicatechin is substantially (−)-epicatechin.

In certain embodiments of anyone of the embodiments disclosed above, said epicatechin is substantially (+)-epicatechin.

In certain embodiments of anyone of the embodiments disclosed above, said epicatechin is a racemic mixture of (−)-epicatechin and (+)-epicatechin.

In certain embodiments of anyone of the embodiments disclosed above, said patient is selected for treatment based on the occurrence of one or more physiological manifestations of skeletal or cardiac muscle injury or dysfunction in the subject.

In further embodiments, said manifestation is elevation in a biomarker selected from the group consisting of elevated plasma levels of myoglobin, troponin, or creatine phosphokinase, lactic acidosis, and creatinine.

In certain embodiments of anyone of the embodiments disclosed above, a diagnostic biomarker is used to determine the time and degree of muscle response.

In further embodiments, said diagnostic biomarker is dystrophin or thrombospondin.

In certain embodiments of anyone of the embodiments disclosed above, epicatechin is administered.

In certain embodiments of anyone of the embodiments disclosed above, an epicatechin derivative is administered.

In further embodiments, said epicatechin, epicatechin derivative, pharmaceutically acceptable salts and prodrugs thereof, or combinations thereof, are administered orally.

In other embodiments, said epicatechin, epicatechin derivative, pharmaceutically acceptable salts and prodrugs thereof, or combinations thereof, are administered parenterally.

In other embodiments, said epicatechin, epicatechin derivative, pharmaceutically acceptable salts and prodrugs thereof, or combinations thereof, are administered as a neutraceutical.

In further embodiments, epicatechin, epicatechin derivatives, pharmaceutically acceptable salts and prodrugs thereof, or combinations thereof, are administered in combination with an additional therapeutics agent. Said additional therapeutic agent is selected from the group consisting of hormones which stimulate muscle cell growth, y-amino butyric acid or its derivatives, dietary protein supplements, anabolic steroids, biological factors known to enhance the growth, strength, endurance, or metabolism of skeletal or cardiac muscle, or recovery of skeletal muscle or cardiac muscle from injury or weakness, compounds known to be associated with increased nitric oxide production which promotes blood flow through muscles, extracts of natural products known to promote muscle strength or endurance, inhibitors of myostatin, and stimulators of follistatin expression.

Also provided herein is a method of diagnosing the degree of severity of a muscle disorder, comprising the step of measuring the plasma levels of follistatin, myostatin, or the ratio of follistatin to myostatin.

Also provided herein is a method of determining the extent of response to therapy for a muscle disorder, comprising the steps of:
  a) measuring the pre-treatment plasma levels of follistatin, myostatin, or the ratio of follistatin to myostatin;
  b) measuring the post-treatment plasma levels of follistatin, myostatin, or the ratio of follistatin to myostatin; and
  c) comparing the pre- and post-treatment levels of follistatin, myostatin, or the ratio of follistatin to myostatin.

Also provided herein is a method of treatment of a muscle disorder, comprising the steps of:
a) measuring the plasma levels of follistatin, myostatin, or the ratio of follistatin to myostatin a first time;
b) administering a first amount of epicatechin (either (+) or (−) enantiomers, or a combination of both), an epicatechin derivative, or a pharmaceutically acceptable salt or prodrug thereof;
c) measuring the post-treatment plasma levels of follistatin, myostatin, or the ratio of follistatin to myostatin;
d) comparing the pre- and post-treatment levels of follistatin, myostatin, or the ratio of follistatin to myostatin; and
e) either:
  i) increasing the dose of epicatechin (either (+) or (−) enantiomers, or a combination of both), an epicatechin derivative, or a pharmaceutically acceptable salt or prodrug thereof administered in step b when the measured follistatin concentration in the subject has increased, when the measured myostatin concentration in the subject has decreased, or when the ratio of plasma follistatin to plasma myostatin has increased; or
  ii) decreasing or maintaining the dose of epicatechin (either (+) or (−) enantiomers, or a combination of both), an epicatechin derivative, or a pharmaceutically acceptable salt or prodrug thereof administered in step b when the measured follistatin concentration in the subject has decreased, when the measured myostatin concentration in the subject has increased, or when the ratio of plasma follistatin to plasma myostatin has decreased.

In certain embodiments of anyone of the embodiments disclosed above, said epicatechin is a racemic mixture of greater than 50% (−)-epicatechin and less than 50% (+)-epicatechin.

In certain embodiments of anyone of the embodiments disclosed above, said a racemic mixture is greater than 75% (−)-epicatechin.

In certain embodiments of anyone of the embodiments disclosed above, said a racemic mixture is greater than 90% (−)-epicatechin.

In certain embodiments of anyone of the embodiments disclosed above, said a racemic mixture is greater than 75% (+)-epicatechin.

In certain embodiments of anyone of the embodiments disclosed above, said a racemic mixture greater than 90% (+)-epicatechin.

Also provided herein is the use of epicatechin, (+)-epicatechin, (−)-epicatechin, a combination of (+)- and (−)-epicatechin, an epicatechin derivative, a pharmaceutically acceptable salt or prodrug of any of the foregoing, or a combination of any of the foregoing, in the manufacture of a medicament for the treatment of any of the diseases, or for the achievement of any therapeutic or functional endpoint, as disclosed herein.

As used herein, the terms below have the meanings indicated.

When ranges of values are disclosed, and the notation "from n, . . . to n," or "between n, . . . and n," is used, where n, and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 uM (micromolar)," which is intended to include 1 uM, 3 uM, and everything in between to any number of significant figures (e.g., 1.255 uM, 2.1 uM, 2.9999 uM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "muscular diseases" refers to diseases associated with impaired skeletal muscle or cardiac muscle cell number or function.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein. In certain embodiments, a combination of compounds is administered such that the clearance half-life of each compound from the body overlaps at least partially with one another. For example, a first pharmaceutical has a clearance half-life of 1 hour and is administered at time=O, and a second pharmaceutical has a clearance half-life of 1 hour and is administered at time=45 minutes.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "epicatechin" as used herein refers to (+)-epicatechin (2R-3R), (−)-epicatechin (2S-3S), or mixtures thereof. In certain embodiments, "epicatechin" refers to (+)-epicatechin. In further embodiments, "epicatechin" refers to (−)-epicatechin. In further embodiments, "epicatechin" refers to a racemic mixture of (+)-epicatechin and (−)-epicatechin.

The term "epicatechin derivative" as used herein refers to any compound which retains the ring structure and stereochemistry of epicatechin itself, but which contains one or more substituent groups relative to epicatechin. Certain naturally occurring epicatechin derivatives are known, such as (−)-epigallocatechin (EGC), (−)-epicatechin-3-gallate (ECG), (−)-epigallocatechin-3-gallate (EGCG), (+)-epigallocatechin (EGC), (+)-epicatechin-3-gallate (ECG), and (+)-epigallocatechin-3-gallate (EGCG). The term also includes combination molecules or prodrugs that release epicatechin or a derivative thereof when administered to a subject. Such a combination molecule may include, for example, epicatechin and an agent joined by a hydrolysable linker group.

Epicatechin and its derivatives may be made synthetically, or may be isolated from natural sources that contain these compounds, such as chocolate, tea, and nuts. The term "chocolate" as used herein refers to a solid or semi-plastic food and is intended to refer to all chocolate or chocolate-like compositions containing a dispersion of solids within a fat phase. The term is intended to include compositions conforming to the U.S. Standards of Identity (SOI), CODEX Alimentarius and/or other international standards and compositions not conforming to the U.S. Standards of Identity or other international standards. The term "chocolate" encompasses sweet chocolate, bittersweet or semisweet chocolate, milk chocolate, buttermilk chocolate, skim milk chocolate, mixed dairy product chocolate, sweet cocoa and vegetable fat coating, sweet chocolate and vegetable fat coating, milk chocolate and vegetable fat coating, vegetable fat based coating, pastels including white chocolate or coating made with cocoa butter or vegetable fat or a combination of these, nutritionally modified chocolate-like compositions (chocolates or coatings made with reduced calorie ingredients), and low fat chocolates, unless specifically identified otherwise. See, e.g., U.S. Pat. No. 6,312,753, which is hereby incorporated by reference herein. By way of example, epicatechin and its derivatives may be delivered by administration of tea extracts, cocoa components, partially and fully defatted cocoa solids, cocoa nibs and fractions derived therefrom, cocoa polyphenol extracts, cocoa butter, chocolate liquors, and mixtures thereof.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VCHA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methane sulfonate, naphthy lenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluene sulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carriers) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Specific sustained release formulations of the compounds disclosed herein are described in U.S. Pat. No. 6,410,052, which is hereby incorporated by reference.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with agents which allow or enhance improvements in the number, structure or function of skeletal muscle cells or cardiac muscle cells.

In further embodiments, such agents include hormones which stimulate muscle cell growth, butyric acid or its derivatives, dietary protein supplements, anabolic steroids, biological factors known to enhance the growth, strength, endurance, or metabolism of skeletal or cardiac muscle, or recovery of skeletal muscle or cardiac muscle from injury or weakness, compounds known to be associated with increased nitric oxide production which promotes blood flow through muscles, extracts of natural products known to promote muscle strength or endurance, inhibitors of myostatin, and stimulators of follistatin expression.

In further embodiments, hormones which stimulate muscle cell growth include, but are not limited to, growth hormone, growth hormone analogs, growth hormone releasing peptides or analogs thereof, growth hormone secretagogues, or other hormones such as somatotropin or mechano growth factor.

In further embodiments butyric acid derivatives include neurotransmitters that benefit muscles by modulating the pituitary gland.

In further embodiments, dietary protein supplements include, but are not limited to, proteins such as casein, amino acids precursors or derivatives thereof with known attributes of potentiating muscle growth, such as leucine, valine, isovaline, beta alanine, glutamine, glutamine dipeptide, or glycocyamine.

In further embodiments anabolic steroids, include, but are not limited to, testosterone or related steroid compounds with muscle growth inducing properties, such as cyclostanazol or methadrostenol, prohormones or derivatives thereof, modulators of estrogen, and selective androgen receptor modulators (SARMS).

In further embodiments, biological factors known to enhance the growth, strength, endurance, or metabolism of skeletal or cardiac muscle, or recovery of skeletal muscle or cardiac muscle from injury or weakness, include, but are not limited to, alpha-lipoic acid, taurine, caffeine, magnesium, niacin, folic acid, ornithine, vitamin B6, B12, or D, aspartate, creatine and its diverse salts such creatine monohydrate, betaine, N-acetyl cysteine, beta-hydroxyl methyl butyrate, lecithin, choline, phospholipid mixtures, phosphatidyl serine, carnitine, L-carnitine, and glycine proprionyl-L-carnitine.

In further embodiments, compounds known to be associated with increased nitric oxide production which promotes blood flow through muscles include, but are not limited to, arginine and citrulline.

In further embodiments, extracts of natural products known to promote muscle strength or endurance, include, but are not limited to, *guarana, Geranium robertianum, Cirsium ologophyllum, Bauhinia purpureae*, Yohimbe, *Bacopa monniera*, beet powder, *rhodiola*, or tea extracts.

In further embodiments, inhibitors of myostatin are proteins, antibodies, peptides, or small molecules.

In further embodiments, stimulators of follistatin expression or function are proteins, peptides, or small molecules.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating muscular diseases in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of muscular diseases.

The compositions of the present invention may also be formulated as neutraceutical compositions. The term "neutraceutical composition" as used herein refers to a food product, foodstuff, dietary supplement, nutritional supplement or a supplement composition for a food product or a foodstuff comprising exogenously added catechin and/or epicatechin. Details on techniques for formulation and administration of such compositions may be found in Remington, The Science and Practice of Pharmacy 21st Edition (Mack Publishing Co., Easton, Pa.) and Nielloud and Marti-Mestres, Pharmaceutical Emulsions and Suspensions: 2nd Edition (Marcel Dekker, Inc, New York).

As used herein, the term food product refers to any food or feed suitable for consumption by humans or animals. The food product may be a prepared and packaged food (e.g., mayonnaise, salad dressing, bread, grain bar, beverage, etc.) or an animal feed (e.g., extruded and pelleted animal feed, coarse mixed feed or pet food composition). As used herein, the term foodstuff refers to any substance fit for human or animal consumption.

Food products or foodstuffs are for example beverages such as nonalcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour).

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form.

The term "dietary supplement" refers to a small amount of a compound for supplementation of a human or animal diet packaged in single or multiple dose units.

Dietary supplements do not generally provide significant amounts of calories but may contain other micronutrients (e.g., vitamins or minerals). The term food products or foodstuffs also includes functional foods and prepared food products pre-packaged for human consumption.

The term nutritional supplement refers to a composition comprising a dietary supplement in combination with a source of calories. In some embodiments, nutritional supplements are meal replacements or supplements (e.g., nutrient or energy bars or nutrient beverages or concentrates).

Dietary supplements of the present invention may be delivered in any suitable format. In certain embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or noncoated), tea, or the like.

In certain embodiments, the dietary supplement is in the form of a tablet or capsule and in further embodiments is in the form of a hard (shell) capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). In certain embodiments, carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate.

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food or the dietary supplement e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provide nutrient calories. In certain embodiments, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In an embodiment, the protein is a combination of whey protein concentrate and calcium caseinate. These proteins have high biological value; that is, they have a high proportion of the essential amino acids. See Modern Nutrition in Health and Disease, 8th ed., Lea & Febiger, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin). Selection of one or several of these ingredients is a matter of formulation, design, consumer preferences and end user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In an embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the neutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the neutraceutical compositions. Examples of suitable emulsifiers include, but are not limited to, lecithin (e.g., from egg or soy), and/or mono and diglycerides. Other emulsifiers are readily apparent to the skilled artisan and selection of suitable emulsifier(s) will depend, in part, upon the formulation and final product. Preservatives may also be added to the nutritional supplement to extend product shelf life. In certain embodiments, preservatives such as potassium sorbate, sodium sorbate, potassium benzoate, sodium benzoate or calcium disodium EDTA are used.

In addition to the carbohydrates described above, the neutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the neutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The dosage and ratios of catechin and/or epicatechin and additional components administered via a neutraceutical will vary depending upon known factors, such as the pharmaceutical characteristics of the particular composition and its mode and route of administration; the age, health and weight of the recipient; the nature and extent of the symptoms; the kind of concurrent treatment; the frequency of treatment; and the effect desired which can determined by the expert in the field with normal trials, or with the usual considerations regarding the formulation of a neutraceutical composition.

It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular disease undergoing therapy, as is well understood by those skilled in the art.

Specific diseases to be treated by the compounds, compositions, and methods disclosed herein include: impaired skeletal and cardiac muscle function, recovery of skeletal or cardiac muscle health or function, functionally significant regeneration of skeletal or cardiac muscle cells or function, and any other diseases disclosed herein.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Biological Activity Assays

Western Blot Assays:

Cells or skeletal muscle tissue samples were homogenized in 50 ul lysis buffer (1% triton X-100, 20 mmol/L Tris, 140 mmol/L NaCl, 2 mmol/L EDTA, and 0.1% SDS) with protease and phosphatase inhibitor cocktails supplemented with 1 mmol/L PMSF, 2 mmol/L $Na_3VO_4$ and 1 mmol/L NaP. Homogenates were passed through an insulin syringe five times, sonicated for 30 min at 4DC and centrifuged (12,000×g) for 10 min. The total protein content was measured in the supernatant. A total of 40)Ig of protein was loaded onto a 5% or 10% SDS-PAGE, electrotransferred, incubated for 1 h in blocking solution (5% nonfat dry milk in TBS plus 0.1% Tween 20 [TBS-T]), followed by either a 3-h incubation at room temperature or overnight incubation at 4DC with primary antibodies. Primary antibodies were typically diluted 1:1000 or 1:2000 in TBS-T plus 5% bovine serum albumin. Membranes were washed (3× for 5 min) in TBS-T and incubated 1 h at room temperature in the presence of HRP-conjugated secondary antibodies diluted 1:10,000 in blocking solution. Membranes were again washed 3 times in TBS-T, and the immunoblots were developed using an enhanced chemiluminescence detection kit. The band intensities were digitally quantified. All primary antibodies are commercially available.

Mouse Myoblast Assay

Epicatechin induces follistatin expression, suppresses myostatin expression and accelerates the differentiation of cultured mouse myoblasts into myotubes. These phenomena are associated with increased expression of biomarkers of muscle differentiation, such as myogenin and myoD. The mouse myoblast cell line, C2C12, was grown to semi-confluence in 6-well tissue culture plates and then exposed to epicatechin (100 nM) for three days using literature-standardized differentiation inducing media: DMEM supplemented with 2% horse serum. Proteins were extracted, separated by conventional gel electrophoresis and stained as Western blots by reacting with commercially available antibodies specific for markers of muscle cell growth and differentiation. In experiments examining the comparative effects of (−) and (+) epicatechin enantiomers on muscle cells, the cells were grown to semi-confluence in 6 well plates, placed into literature-standardized differentiation medium containing horse serum, and then stimulated for 24 hours with (−) or (+) epicatechin enantiomers, at concentrations ranging from 10 nM to 1000 nM. The cells were then harvested as above, and Western blots were prepared to determine relative expression of PGCla and follistatin, using commercially available, specific, primary antibodies.

Treatment of Diabetic Patients with Epicatechin-Rich Cocoa Products

Five patients with type 2 diabetes and heart failure were provided epicatechin-rich cocoa products (providing −100 mg epicatechiniday) every day for three months.

Epicatechin rich cocoa increased protein levels of the stimulator of skeletal muscle growth, follistatin, markers of muscle differentiation, (myogenin, myoD) and suppressed the expression of the inhibitory protein, myostatin in biopsy samples of human skeletal muscle after three months of treatment. Patients underwent biopsies of their quadriceps muscle before and after completing treatment. The biopsy material was analyzed by Western blots for the analysis of muscle protein content.

Electron micrographs of quadriceps muscle biopsy samples obtained before and after three months of treatment show a severe disruption and distortion of sarcomere ultrastructure in human skeletal muscle of diabetic patients with heart failure, consistent with sarcopenia. Treatment significantly restored sarcomere organization of skeletal muscle to near normal. This phenomenon was evidenced in all five patients as average histology score improved significantly.

Treatment with epicatechin induced increased expression of the activated form (de-acetylated) of PGC 1a, a transcriptional regulator of muscle repair and regeneration, as well as mitochondrial biogenesis, in the patients' quadriceps muscles. Treatment also increased the expression of elements of the sarcoglycan protein family, including dystrophin, dysferlin, and utrophin, consistent with the observed improvement in sarcomere morphology. Treatment also increased mitochondrial biogenesis, as evidenced by increased Electron Transport Complex proteins per mg of quadriceps tissue.

Baseline skeletal muscle thiol levels (by using a Cayman Inc. gluthatione assay kit) in diabetic patients with heart failure manifested a marked decrease evidencing significant tissue oxidative stress as compared to normal muscle. Treatment with epicatechin rich cocoa restored total thiol levels, an indication of a normalization of tissue oxidative stress levels. Epicatechin treatment also increased quadriceps expression of superoxide dismutase and catalase, important enzymes that protect against oxidative muscle injury.

In-Vivo Studies in Wild Mice and a Mouse Model of Muscular Dystrophy

Wild type (i.e. normal) and delta sarcoglycan (δ-SG) null mice which develop muscular dystrophy were treated by oral gavage for 30 days with epicatechin at 1 mg/kg twice a day, obtained from Sigma-Aldrich, or with water only (Control). Quadriceps muscle protein samples were analyzed by Western blots to assess for changes in protein levels of the mitochondrial proteins porin, mitofilin, complex V (CV), superoxide dismutase 2 (SOD2), and catalase. In wild type mice, epicatechin treatment increases and in δ-SG null mice prevents the loss of mitochondrial proteins. In the muscular dystrophy mice, epicatechin increased the protein expression of both catalase and superoxide dismutase 2 in the heart and quadriceps muscle, important enzymes that counter the damaging effects of oxidation injury by decreasing the severity of oxidation injury.

Delta sarcoglycan (δ-SG) muscular dystrophy mice exhibit reduced glutathione content (GSH, by using a Cayman Inc. gluthatione assay kit) in quadriceps muscle, evidencing enhanced tissue oxidative stress. Epicatechin treatment markedly increased muscle GSH levels in both wild type mice and delta sarcoglycan knock-out mice.

Delta sarcoglycan knock-out muscular dystrophy mice demonstrated a marked increase in PGC 1a, a transcriptional factor that regulates muscle repair and regeneration, and regulates mitochondrial biogenesis, in skeletal muscle after treatment with oral epicatechin, 1 mg/kg twice a day for 4 weeks.

In one experiment, elderly wild type mice (26 months) with the muscle impairment of the elderly were treated for 2 weeks with epicatechin, 1 mg/kg twice a day for two weeks. They also demonstrated a significant increase in PGC1u in the skeletal muscle, with a correlative increase in mitochondrial protein expression.

In one experiment, mdx mice, characterized by the same dystrophin mutation as is seen with Duchenne's muscular dystrophy, were treated orally with epicatechin, 1 mg/kg twice a day for 4 weeks. They demonstrated an increase in muscle strength compared to controls treated with water, as determined by a standard timed hanging upside down test.

In the mouse myocyte cell line, C2C12, both (−) and (+) epicatechin enantiomers stimulated the expression of PGC1u and follistatin within 24 hr, consistent with activation of transcriptional pathways regulating muscle regeneration and expression of the muscle trophic hormone, follistatin.

Biomarkers

The induction of follistatin, a muscle growth hormone and suppression of myostatin, an inhibitor of muscle growth, by epicatechin in vitro and in vivo suggest that these proteins might be useful biomarkers in monitoring the effects of epicatechin in vivo. In diabetic patients with heart failure, the ratio of follistatin to myostatin was measured and calculated before and after treatment with epicatechin rich cocoa. There was a statistically significant increase in the follistatin/myostatin ratio associated with treatment, indicating an increase in follistatin and a decrease in its natural antagonist, myostatin.

Effect on Body Growth

SD rats of the body weight 50-60 g and age 3-4 weeks were divided into 4 groups. Group A animals were part of vehicle control group, Group B animals were administered Dexamethasone daily; Group C animals were dosed Epicatechin 3 mg/kg followed by dosing of Dexamethasone; Group D animals were dosed 10 mg/kg Epicatechin followed by Dexamethasone. All dosing were by subcutaneous (SC) mode of administration. Dosing of animals was continued for 36 days. Body weight was measured every alternate day, overall length was measured weekly. Animals were photographed periodically to further support data. Feed intake, general health and movement were assessed routinely. On 37$^{th}$ day animals were sacrificed and femur and tibia length were measured using Vernier Calipers. Blood was collected and stored.

It has been confirmed that follistatin can have a beneficial ameliorating effect on the decrease in body growth associated with the inhibition of bone formation secondary to the toxicity of corticosteroids, as shown in Table 1 below.

TABLES 1-3

Data on growth of 4-week rates on dexamethasone with or without additional concurrent treatment with epicatechin.

| | | | | Dex = 1.5 mpk | | Dex = 1 mpk | | Dex = 0.5 mpk | |
|---|---|---|---|---|---|---|---|---|---|
| | WEIGHT (g) | Day 1 | | Day 11 | | Day 23 | | Day 35 | |
| Rat. No | Group | Ind | Avg | Ind | Avg | Ind | Avg | Ind | Avg |
| 1 | CONTROL | 58.2 | 61.2 | 123.9 | 132.3 | 211.2 | 220.7 | 302.8 | 318.4 |
| 2 | | 64.2 | | 140.7 | | 230.2 | | 333.9 | |
| 3 | DEX | 55.4 | 59.3 | 91.1 | 89.1 | 88.0 | 85.7 | 103.9 | 96.1 |
| 4 | | 57.7 | | 84.3 | | 80.0 | | 93.1 | |
| 5 | | 64.8 | | 91.9 | | 89.0 | | 91.5 | |
| 6 | DEX + EPI(3) | 59.9 | 59.2 | 85.6 | 84.8 | 104.0 | 103.5 | 185.1 | 183.3 |
| 7 | | 55.4 | | 81.2 | | 105.2 | | 181.7 | |
| 8 | | 62.2 | | 87.6 | | 101.3 | | 183.1 | |

TABLES 1-3-continued

Data on growth of 4-week rates on dexamethasone with or without additional concurrent treatment with epicatechin.

| 9 | DEX + EPI(10) | 54.6 | 60.3 | 76.9 | 86.1 | 93.3 | 103.8 | 189.4 | 199.3 |
|---|---|---|---|---|---|---|---|---|---|
| 10 | | 65.9 | | 95.3 | | 114.3 | | 209.1 | |

| | | Dex = 1.5 mpk | | Dex = 1 mpk | | Dex = 0.5 mpk | | | |
|---|---|---|---|---|---|---|---|---|---|
| LENGTH (cm) | | Day 1 | | Day 13 | | Day 23 | | Day 35 | |
| Rat. No | Group | Ind | Avg | Ind | Avg | Ind | Avg | Ind | Avg |
| 1 | CONTROL | #DIV/0! | | 17.4 | 17.1 | 18.0 | 18.3 | 21.5 | 20.8 |
| 2 | | | | 16.7 | | 18.5 | | 20 | |
| 3 | DEX | #DIV/0! | | 15.4 | 15.3 | 14.5 | 14.2 | 14.5 | 14.2 |
| 4 | | | | 15.1 | | 14.0 | | 14 | |
| 5 | | | | 15.3 | | 14.0 | | 14 | |
| 6 | DEX + EPI(3) | #DIV/0! | | 15.2 | 15.1 | 15.0 | 14.8 | 17.5 | 17.7 |
| 7 | | | | 15.1 | | 15.0 | | 17.5 | |
| 8 | | | | 15.1 | | 14.5 | | 18 | |
| 9 | DEX + EPI(10) | #DIV/0! | | 14.5 | 14.9 | 15.5 | 15.5 | 18.5 | 18.8 |
| 10 | | | | 15.2 | | 15.5 | | 19 | |

| Bone Length (mm) | | |
|---|---|---|
| Groups | Femur Length (mm) | Tibia Length (mm) |
| Group 1 - Vehicle Control | 32.30 | 40.89 |
| Group 2 - Dexas/c | 22.68 | 28.67 |
| Group 3 - Epi 1 - 3 MPK s/c | 29.57 | 34.91 |
| Group 4 - Epi 1 - 10 MPK s/c | 31.30 | 35.37 |

What is claimed is:

1. A method of increasing expression of one or more proteins selected from the group consisting of the sarcoglycan family of proteins, dystrophin, dysferlin, and utrophin in a subject in need thereof, comprising administering to the subject a therapeutically effective amount of (+)–epicatechin and/or (–)–epicatechin, an epicatechin derivative of either (+)–epicatechin or (–)–epicatechin, or a pharmaceutically acceptable salt thereof, wherein the therapeutically effective amount is obtained by detecting increased expression of a protein comprising an activated form of PGC1a in an assay.

2. The method of claim 1, wherein the one or more proteins comprise dystrophin.

3. The method of claim 1, wherein the one or more proteins comprise dysferlin.

4. A method for reversal or amelioration of a disease or condition characterized by deficient expression of one or more proteins selected from the group consisting of the sarcoglycan family of proteins, dystrophin, dysferlin, and utrophin in a subject in need thereof, comprising administering to the subject a therapeutically effective amount of (+)–epicatechin and/or (–)–epicatechin, an epicatechin derivative of either (+)–epicatechin or (–)–epicatechin, or a pharmaceutically acceptable salt thereof wherein the therapeutically effective amount is obtained by detecting increased expression of a protein comprising an activated form of PGC1a in an assay.

5. The method of claim 4, wherein the one or more proteins comprise dystrophin.

6. The method of claim 4, wherein the one or more proteins comprise dysferlin.

7. The method of claim 4, wherein the disease or condition is muscular dystrophy.

8. The method of claim 4, wherein the disease or condition is Duchenne's muscular dystrophy.

9. The method of claim 4, wherein the disease or condition is sarcopenia, muscle weakness, or muscle atrophy.

10. The method of claim 9, wherein the sarcopenia, muscle weakness, or muscle atrophy is secondary to aging, diabetes, a metabolic disorder, an infection, inflammation, an autoimmune disease, cardiac dysfunction, a disuse syndrome, inactivity associated with arthritis, injury, or injury associated with medication.

11. The method of claim 10, wherein the sarcopenia, muscle weakness, or muscle atrophy is secondary to injury caused by medication, wherein the medication is cancer chemotherapy or a corticosteroid.

12. The method of claim 4, wherein the disease or condition is skeletal muscle injury.

13. The method of claim 4, wherein the disease or condition is a peripheral denervation syndrome.

14. A method of improving deficient muscle function, or reversing a state of muscle weakness due to deficient expression of one or more proteins selected from the group consisting of the sarcoglycan family of proteins, dystrophin, dysferlin, and utrophin in a subject in need thereof, comprising administering to the subject a therapeutically effective amount of (+)–epicatechin and/or (–)–epicatechin, an epicatechin derivative of either (+)–epicatechin or (–)–epicatechin, or a pharmaceutically acceptable salt thereof, wherein the therapeutically effective amount is obtained by detecting increased expression of a protein comprising an activated form of PGC1a in an assay.

15. The method of claim 14, wherein the one or more proteins comprise dystrophin.

16. The method of claim 14, wherein the one or more proteins comprise dysferlin.

17. The method of claim 1, wherein the (+)–epicatechin and/or (–)–epicatechin, the epicatechin derivative, or the pharmaceutically acceptable salt thereof, is administered orally or intravenously or intramuscularly, at 5 mg to 2 grams per day, in a single dose or in divided doses.

18. The method of claim 4, wherein the (+)–epicatechin and/or (–)–epicatechin, the epicatechin derivative, or the pharmaceutically acceptable salt thereof, is administered orally or intravenously or intramuscularly, at 5 mg to 2 grams per day, in a single dose or in divided doses.

19. The method of claim 14, wherein the (+)-epicatechin and/or (−)-epicatechin, the epicatechin derivative, or the pharmaceutically acceptable salt thereof, is administered orally, intravenously or intramuscularly, at 5 mg to 2 grams per day, in a single dose or in divided doses.

20. The method of claim 1, wherein the (+)-epicatechin and/or the (−)-epicatechin, the epicatechin derivative, or the pharmaceutically acceptable salt thereof, is administered at a dose between 0.1 mg/kg of bodyweight per day to 10 mg/kg of bodyweight per day, orally, intravenously or intramuscularly, in a single dose or in divided doses.

21. The method of claim 4, wherein the (+)-epicatechin and/or the (−)-epicatechin, the epicatechin derivative, or the pharmaceutically acceptable salt thereof, is administered at a dose between 0.1 mg/kg of bodyweight per day to 10 mg/kg of bodyweight per day, orally, or intravenously or intramuscularly, in a single dose or in divided doses.

22. The method of claim 14, wherein the (+)-epicatechin and/or the (−)-epicatechin, the epicatechin derivative, or the pharmaceutically acceptable salt thereof, is administered at a dose between 0.1 mg/kg of bodyweight per day to 10 mg/kg of bodyweight per day, orally, intravenously or intramuscularly, in a single dose or in divided doses.

23. The method of claim 1, wherein the method comprises administering to the subject a therapeutically effective amount of (+)-epicatechin and/or (−)-epicatechin.

24. The method of claim 4, wherein the method comprises administering to the subject a therapeutically effective amount of (+)-epicatechin and/or (−)-epicatechin.

25. The method of claim 14, wherein the method comprises administering to the subject a therapeutically effective amount of (+)-epicatechin and/or (−)-epicatechin.

26. The method of claim 1, wherein the method comprises administering to the subject a therapeutically effective amount of (+)-epicatechin and/or (−)-epicatechin, wherein at least 75% of the total amount of epicatechin is (+)-epicatechin.

27. The method of claim 4, wherein the method comprises administering to the subject a therapeutically effective amount of (+)-epicatechin and/or (−)-epicatechin, wherein at least 75% of the total amount of epicatechin is (+)-epicatechin.

28. The method of claim 14, wherein the method comprises administering to the subject a therapeutically effective amount of (+)-epicatechin and/or (−)-epicatechin, wherein at least 75% of the total amount of epicatechin is (+)-epicatechin.

29. The method of claim 1, wherein the administration increases cellular, muscular, or bodily production of follistatin.

30. The method of claim 4, wherein the (+)-epicatechin and/or (−)-epicatechin, the epicatechin derivative, or the pharmaceutically acceptable thereof, is administered orally, intravenously or intramuscularly, at 25 to 200 mg per day, in a single dose or in divided doses.

31. The method of claim 4, wherein the (+)-epicatechin and/or the (−)-epicatechin, the epicatechin derivative, or the pharmaceutically acceptable salt thereof, is administered at a dose between 0.1 mg/kg of bodyweight per day to 500 mg/kg of bodyweight per day, orally, or intravenously or intramuscularly, in a single dose or in divided doses.

32. A method for reversal or amelioration of a disease or condition characterized by deficient expression of one or more proteins selected from the group consisting of the sarcoglycan family of proteins and dystrophin in a subject in need thereof, comprising administering to the subject a therapeutically effective amount of (+)-epicatechin and/or (−)-epicatechin, an epicatechin derivative of either (+)-epicatechin or (−)-epicatechin, a pharmaceutically acceptable salt thereof, wherein the therapeutically effective amount is obtained by detecting increased expression of a protein comprising an activated form of PGC1a in an assay.

33. The method of claim 32, wherein the one or more proteins comprise dystrophin.

34. The method of claim 32, wherein the disease or condition is muscular dystrophy.

35. The method of claim 32, wherein the (+)-epicatechin and/or (−)-epicatechin, the epicatechin derivative, or the pharmaceutically acceptable salt thereof, is administered orally, or intravenously or intramuscularly, at 5 mg to 2 grams per day, in a single dose or in divided doses.

36. The method of claim 32, wherein the (+)-epicatechin and/or (−)-epicatechin, the epicatechin derivative, or the pharmaceutically acceptable salt thereof, is administered orally, or intravenously or intramuscularly, at 25 to 200 mg per day, in a single dose or in divided doses.

37. The method of claim 32, wherein the method comprises administering to the subject a therapeutically effective amount of (+)-epicatechin and/or (−)-epicatechin.

38. The method of claim 32, wherein the method comprises administering to the subject a therapeutically effective amount of (+)-epicatechin and/or (−)-epicatechin, wherein at least 75% of the total amount of epicatechin is (+)-epicatechin.

* * * * *